US012447003B2

(12) United States Patent
King et al.

(10) Patent No.: US 12,447,003 B2
(45) Date of Patent: Oct. 21, 2025

(54) BRANCHING STENT GRAFT WITH MECHANICAL INTERLOCK

(71) Applicant: Medtronic Vascular, Inc., Santa Rosa, CA (US)

(72) Inventors: Haley King, Santa Rosa, CA (US); Adam Shipley, Santa Rosa, CA (US); Timothy Bertini, Santa Rosa, CA (US); Ana Zavala, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 17/950,503

(22) Filed: Sep. 22, 2022

(65) Prior Publication Data

US 2023/0081550 A1 Mar. 16, 2023

Related U.S. Application Data

(62) Division of application No. 16/837,527, filed on Apr. 1, 2020, now Pat. No. 11,471,264.

(51) Int. Cl.
*A61F 2/07* (2013.01)
*A61F 2/06* (2013.01)
*A61F 2/962* (2013.01)

(52) U.S. Cl.
CPC .......... *A61F 2/07* (2013.01); *A61F 2002/067* (2013.01); *A61F 2210/0014* (2013.01); *A61F 2250/0039* (2013.01); *A61F 2250/0063* (2013.01)

(58) Field of Classification Search
None
See application file for complete search history.

(56) References Cited

U.S. PATENT DOCUMENTS 5,064,435 A * 11/1991 Porter ........................ A61F 2/90 606/198
5,383,892 A 1/1995 Cardon et al.
5,562,724 A * 10/1996 Vorwerk .................. A61F 2/07 606/198

(Continued)

FOREIGN PATENT DOCUMENTS

CN 107920883 A * 9/2016
WO 0074598 A1 12/2000
WO 02078569 A2 10/2002

OTHER PUBLICATIONS

PCT/US2021/024251, International Search Report and Written Opinion of the International Searching Authority, mailed Jul. 12, 2021, 9 pages.

*Primary Examiner* — Ann Hu
(74) *Attorney, Agent, or Firm* — Brooks Kushman P.C.

(57) ABSTRACT

The techniques of this disclosure generally relate to a modular assembly including first and second stent-grafts. The first stent-graft includes a body portion having a first diameter and a waist portion having a second diameter less than the first diameter. The waist portion is at a distal end of the first stent-graft. The second stent-graft includes a captured proximal portion configured to be located within the first stent-graft. The captured proximal portion includes a seated portion configured to be located proximal to the waist portion. The seated portion has a third diameter greater than the second diameter to form a mechanical interlock between the first stent-graft and the second stent-graft.

11 Claims, 5 Drawing Sheets

(56) References Cited

U.S. PATENT DOCUMENTS

| | | | | |
|---|---|---|---|---|
| 5,609,627 | A * | 3/1997 | Goicoechea | A61F 2/90 606/108 |
| 5,628,788 | A * | 5/1997 | Pinchuk | A61F 2/07 623/1.2 |
| 5,632,763 | A * | 5/1997 | Glastra | A61F 2/07 606/198 |
| 5,639,278 | A * | 6/1997 | Dereume | A61F 2/07 623/1.13 |
| 5,653,747 | A | 8/1997 | Dereume | |
| 5,662,675 | A * | 9/1997 | Polanskyj Stockert | A61F 2/954 606/194 |
| 5,683,449 | A * | 11/1997 | Marcade | A61F 2/07 606/191 |
| 5,755,773 | A * | 5/1998 | Evans | A61B 17/12022 606/194 |
| 5,758,562 | A | 6/1998 | Thompson | |
| 5,769,884 | A | 6/1998 | Solovay | |
| 5,824,037 | A * | 10/1998 | Fogarty | A61F 2/07 623/1.13 |
| 5,824,040 | A * | 10/1998 | Cox | A61F 2/90 623/1.35 |
| 5,843,160 | A * | 12/1998 | Rhodes | A61F 2/07 623/1.35 |
| 5,957,974 | A | 9/1999 | Thompson et al. | |
| 5,984,955 | A * | 11/1999 | Wisselink | A61F 2/954 623/1.35 |
| 6,030,415 | A * | 2/2000 | Chuter | A61F 2/07 623/1.13 |
| 6,045,557 | A * | 4/2000 | White | A61F 2/958 606/108 |
| 6,159,239 | A | 12/2000 | Greenhalgh | |
| 6,293,969 | B1 | 9/2001 | Chuter | |
| 6,348,066 | B1 * | 2/2002 | Pinchuk | A61F 2/07 606/198 |
| 6,361,557 | B1 * | 3/2002 | Gittings | A61F 2/07 606/151 |
| 6,551,350 | B1 | 4/2003 | Thornton et al. | |
| 6,576,009 | B2 * | 6/2003 | Ryan | A61F 2/90 623/1.35 |
| 6,648,913 | B1 * | 11/2003 | Yee | A61F 2/07 623/1.35 |
| 6,652,580 | B1 * | 11/2003 | Chuter | A61F 2/07 623/1.36 |
| 7,135,037 | B1 * | 11/2006 | Chuter | A61F 2/07 623/1.1 |
| 7,226,474 | B2 * | 6/2007 | Lancea | A61F 2/856 623/1.13 |
| 7,666,221 | B2 | 2/2010 | Escano | |
| 7,682,380 | B2 | 3/2010 | Thornton et al. | |
| 7,927,367 | B2 | 4/2011 | Chuter | |
| 7,998,187 | B2 | 8/2011 | Hartley et al. | |
| 8,177,833 | B2 | 5/2012 | Chuter et al. | |
| 8,337,547 | B2 | 12/2012 | Iancea et al. | |
| 8,628,567 | B1 | 1/2014 | Chuter et al. | |
| 9,107,743 | B2 | 8/2015 | Iancea et al. | |
| 9,839,510 | B2 * | 12/2017 | Shalev | A61F 2/07 |
| 9,949,852 | B2 | 4/2018 | Orion et al. | |
| 10,034,784 | B2 | 7/2018 | Tang | |
| 10,905,540 | B2 * | 2/2021 | Zigelboim | A61F 2/962 |
| 2003/0040772 | A1 | 2/2003 | Hyodoh et al. | |
| 2005/0055082 | A1 * | 3/2005 | Ben Muvhar | A61F 2/91 623/1.15 |
| 2005/0220848 | A1 | 10/2005 | Bates | |
| 2005/0228484 | A1 * | 10/2005 | Stephens | A61F 2/848 623/1.21 |
| 2005/0240261 | A1 * | 10/2005 | Rakos | A61F 2/88 623/1.51 |
| 2006/0155359 | A1 * | 7/2006 | Watson | A61F 2/07 623/1.13 |
| 2006/0178726 | A1 | 8/2006 | Douglas | |
| 2006/0247761 | A1 | 11/2006 | Greenberg et al. | |
| 2009/0171435 | A1 | 7/2009 | Kuppurathanam et al. | |
| 2009/0187240 | A1 | 7/2009 | Clerc et al. | |
| 2010/0094404 | A1 | 4/2010 | Greenhalgh et al. | |
| 2010/0145434 | A1 | 6/2010 | Thornton et al. | |
| 2012/0277850 | A1 | 11/2012 | Bertini | |
| 2015/0374483 | A1 | 12/2015 | Janardhan et al. | |
| 2016/0278910 | A1 | 9/2016 | Kelly | |
| 2017/0224469 | A1 | 8/2017 | Kerr | |
| 2018/0296222 | A1 | 10/2018 | Hebert et al. | |
| 2018/0325702 | A1 | 11/2018 | Tang | |
| 2019/0070028 | A1 | 3/2019 | Bar et al. | |

* cited by examiner

BRANCHING STENT GRAFT WITH MECHANICAL INTERLOCK

This application is a divisional of U.S. patent application Ser. No. 16/837,527 filed on Apr. 1, 2020, and issued as U.S. Pat. No. 11,471,264 on Oct. 18, 2022, entitled "BRANCHING STENT GRAFT WITH MECHANICAL INTERLOCK" of King et al., which is incorporated herein by reference in its entirety

FIELD

The present technology is generally related to endovascular devices, for example, devices for treatment of a diseased aorta.

BACKGROUND

A conventional stent-graft typically includes a radially expandable reinforcement structure, e.g., formed from a plurality of annular stein rings, and a cylindrically shaped layer of graft material defining a lumen to which the stent rings are coupled. Endovascular aneurysmal exclusion is a method of using a stent-graft to exclude pressurized fluid flow from the interior of an aneurysm, thereby reducing the risk of rupture of the aneurysm and the associated invasive surgical intervention.

In complex anatomies, stent-grafts are connected to one another to form a modular assembly. Typically, a first stent-graft is deployed. Stents of a proximal portion of a second stent-graft are then deployed in a distal portion of the first stent-graft. The stents of the second stent-graft press outwards on the interior of the first stent-graft providing an interference fit connection to connect the first and second stent-graft together. However, the interference fit connection can fail over time undesirably allowing the second stent-graft to migrate relative to the first stent-graft.

SUMMARY

The techniques of this disclosure generally relate to a modular assembly including first and second stent-grafts. The first stent-graft includes a body portion having a first diameter and a waist portion having a second diameter less than the first diameter. The waist portion is at a distal end of the first stent-graft. The second stent-graft includes a captured proximal portion configured to be located within the first stent-graft. The captured proximal portion includes a seated portion configured to be located proximal to the waist portion. The seated portion has a third diameter greater than the second diameter of the waist portion to form a mechanical interlock between the first stent-graft and the second stent-graft.

In one aspect, the present disclosure provides a modular assembly includes a first stent-graft having a body portion and a waist portion. The body portion has a first diameter when the first stent-graft is in an expanded configuration. The waist portion has a second diameter when the first stent-graft is in the expanded configuration less than the first diameter. The body portion is configured to expand more than the waist, portion during expansion of the first stent-graft. The modular assembly further includes a second stent-graft including a captured proximal portion located within the first stent-graft. The captured proximal portion includes a seated portion located proximal to the waist portion, the seated portion having the first diameter.

In another aspect, the present disclosure provides a method includes expanding a first stent-graft within a vessel such that a body portion of the first stent-graft has a first diameter and a waist portion of the first stent-graft has a second diameter less than the first diameter. During the expanding, the body portion expands more than the waist portion. The method further includes expanding a seated portion of a second stent-graft within the first stent-graft proximal to the waist portion.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
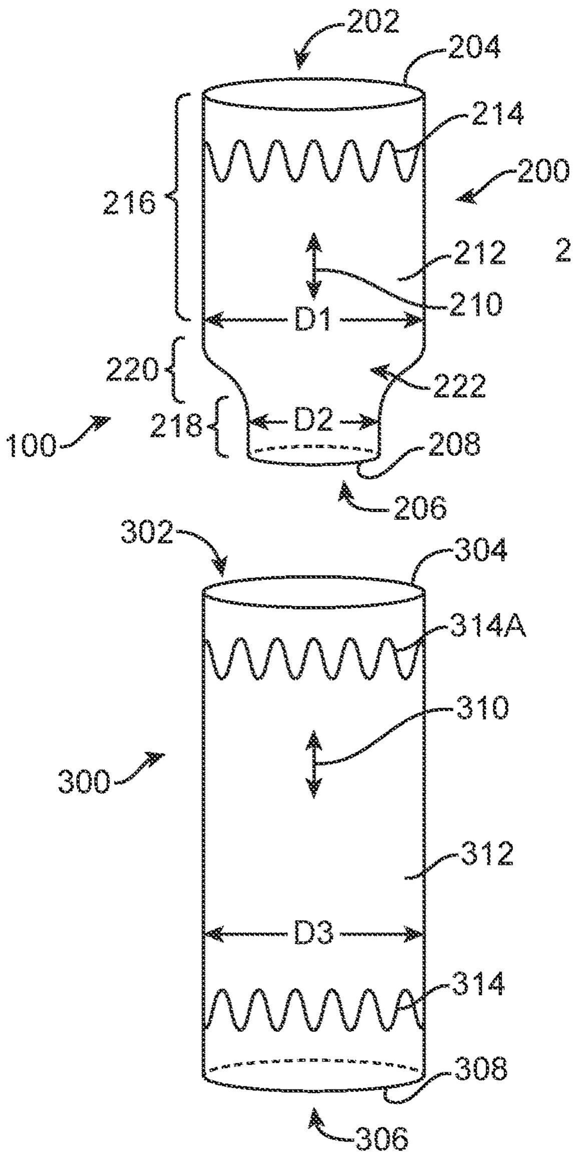
FIG. 1 is a perspective view of a modular assembly including a first stent-graft and a second stent-graft in accordance with one embodiment.

FIG. 1 is a perspective view of a modular assembly 100 including a first stent-graft 200 and a second stent-graft 300 in accordance with one embodiment. Stent-graft 200, sometimes called a vascular implant, is a generally tubular structure having a proximal opening 202 at a proximal end 204 and a distal opening 206 at a distal end 208. As used herein, the proximal end of a stent-graft such as stent-grafts 200, 300 is the end closest to the heart via the path of blood flow whereas the distal end is the end furthest away from the heart during deployment.

Stent-graft 200 defines a lumen 210 extending therethrough from proximal opening 202 to distal opening 206. Stent-graft 200 includes a graft material 212 and one or more stents 214 attached to graft material 212. In one embodiment, stents 214 may include a plurality of spaced apart individual stent rings which are generally sinusoidal, although only a single stent 214 is illustrated. Alternatively, there may be a single, continuous stent (e.g., a helical stent) or a combination of stent rings and continuous stents. Stents 214 may be self-expanding structures, formed of nickel titanium alloy (nitinol), or other shaped memory material, or they may be balloon expandable stents. Graft material 212 may be any suitable graft material known to be utilized in vascular grafts. For example, graft material 212 may be a non-permeable material, e.g., a polyester terephthalate (PET), expanded polyester terephthalate (ePET), or polytetrafluoroethylene (PTFE) based material, or other non-permeable graft material.

Stent-graft 200 includes a body portion 216, a waist portion 218, and a transition portion 220 between body portion 216 and waist portion 218. A first diameter D1 of body portion 216 is greater than a second diameter D2 of waist portion 218. Transition portion 220 has a varying diameter transitioning from first diameter D1 at body portion 216 to second diameter D2 at waist portion 218.

In accordance with this embodiment, body portion 216 extends distally from proximal end 204 to transition portion 220. Waist portion 218 extends proximally from distal end 208 to transition portion 220. Transition portion 220 extends between and connects body portion 216 and waist portion 218. Although waist portion 218 is illustrated at being at distal end 208, in other embodiments, waist portion 218 is spaced apart from distal end 208.

Transition portion 220 and waist portion 218 define a mechanical interlock structure 222, sometimes called an interference lock, of stent-graft 200. Body portion 216 and waist portion 218 are sometimes called an unconstrained stent-graft section and a constrained stent-graft section, respectively.

Stent-graft 200 is illustrated in a deployed configuration where stent-graft 200 is pressurized by a source such as a balloon, a balloon expandable stent, a self-expanding stent, or other expansion to assume the form described and illustrated. While stent-graft 200 is shown as a standalone component, it may also be a portion of a larger stent-graft, such as a leg, limb, or branch of a bifurcated or multi-branch (e.g., two or more lumen) device. One example of this is shown and described with respect to FIG. 15, below.

Stent-graft 300, sometimes called a vascular implant, is a generally tubular structure having a proximal opening 302 at a proximal end 304 and a distal opening 306 at a distal end 308. Stent-graft 300 defines a lumen 310 extending therethrough from proximal opening 302 to distal opening 306.

Stent-graft 300 includes a graft material 312 and one or more stents 314 attached to graft material 312. At least one stent 314A of stents 314 is attached to graft material 312 at or adjacent proximal end 304. Graft material 312 and stents 314 are similar to graft material 212 and stents 214 as discuss above and so the description is not repeated here.

In the embodiment shown, stent-graft 300 is cylindrical having a uniform diameter D3 between proximal end 304 and distal end 308. However, in other embodiments, stent-graft 300 varies in diameter, e.g., flares or tapers at distal end 306. In one specific embodiment, the portion of stent-graft 300 to be inserted within stent-graft 200 has diameter D3 greater than diameter D2 of waist portion 218 to provide a mechanical interlock as discussed below in reference to FIG. 2. In one embodiment, diameter D3 is greater than or equal to diameter D1 of body portion 216.

Figure 2:
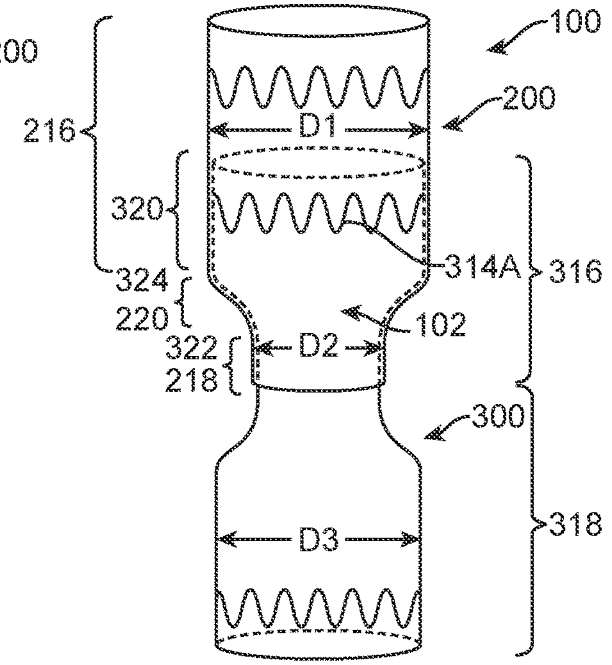
FIG. 2 is a perspective view of the modular assembly of FIG. 1 with the second stent-graft mechanically interlocked with the first stent-graft in accordance with one embodiment.

FIG. 2 is a perspective view of modular assembly 100 of FIG. 1 with stent-graft 300 mechanically interlocked with stent-graft 200 in accordance with one embodiment. As illustrated in FIG. 2, a captured proximal portion 316 of stent-graft 300 is located within stent-graft 200 and a free distal portion 318 of stent-graft 300 extends distally from stent-graft 200.

Captured proximal portion 316 of stent-graft 300 follows the profile of stent-graft 200. More particularly, captured proximal portion 316 includes a seated portion 320, a neck portion 322, and a transition portion 324. Seated portion 320 includes stent 314A and presses outward and engages body portion 216 of stent-graft 200. Accordingly, seated portion 320 has diameter D1 of body portion 216.

Neck portion 322 is a narrow region of stent-graft 300 that is radially constrained by waist portion 218 of stent-graft 200. Neck portion 322 presses outward and engages waist portion 218 of stent-graft 200 and thus has diameter D2 of waist portion 218.

Transition portion 324 presses outward and engages transition portion 220 of stent-graft 200. Accordingly, transition portion 324 of has a varying diameter transitioning from first diameter D1 at seated portion 320 to second diameter D2 at neck portion 322.

Although seated portion 320, neck portion 322, and transition portion 324 are described as having the same diameters as body portion 216, waist portion 218, and transition portion 220, respectively, it is to be understood that the portions overlap one another as described above and so the diameters are essentially equal but slightly different, e.g., by the thickness of the graft material.

By locating seated portion 320 of second stent-graft 300 proximal to waist portion 218 of first stent-graft 200, an interlock 102 is created between stent-grafts 200, 300. Interlock 102 is sometimes called a mechanical interlock, a modular connection, a joint, or overlap region, where two vascular implants mate to treat a diseased region as discussed further below. Stent-graft 200 has a decreased diameter D2 at waist portion 218 in the direction (distal direction) in which force is applied resulting in a higher force required to separate stent-grafts 200, 300, i.e., a higher joint strength. This higher joint strength provides a more robust design for handling in vitro forces preventing clinical hazards and requires less material and length to achieve an appropriate force.

Less material helps with reducing packing density of a loaded system allowing for a small profile thus expanding the treatable population. Less length required to achieve sufficient joint strength also allows for less material coverage of a vessel such as the aorta to achieve the same treatment which allows the modular assembly 100 to treat anatomies that require short lengths, e.g., treating branching vessels. Further, less length also reduces the amount of coverage of the vessel reducing the likelihood of branching vessels being sacrificed and the associated complications, e.g., covering multiple branching vessels may lead to paralysis.

Further, another benefit of starting at a smaller size and requiring a secondary action to create two different diameter shape of stent-graft 200 helps in reducing material for a lower profile system and improves fluid dynamics by reducing the amount of length requiring oversizing of vascular implants that can undesirably obstruct the vessel lumen and increase the likelihood of lumen occlusion. Also, a smoother lumen transition is formed by maximizing the amount of cross-sectional area.

More particularly, the larger diameter D1 of seated portion 320 prevents seated portion 320 from being pulled though the smaller diameter D2 of waist portion 218 thus creating interlock 102 which mechanically locks stein-grafts 200, 300 together. Accordingly, migration of stent-graft 300 with respect to stent-graft 200 is prevented. This, in turn, avoids endoleaks and other complications associated with migration of stent-graft 300.

As described above, transition portion 220 of stent-graft 200 is a smooth transition between body portion 216 and waist portion 218. In other embodiments such as those discussed below in reference to FIGS. 3 and 4, a transition portion can take other forms.

Figure 3:
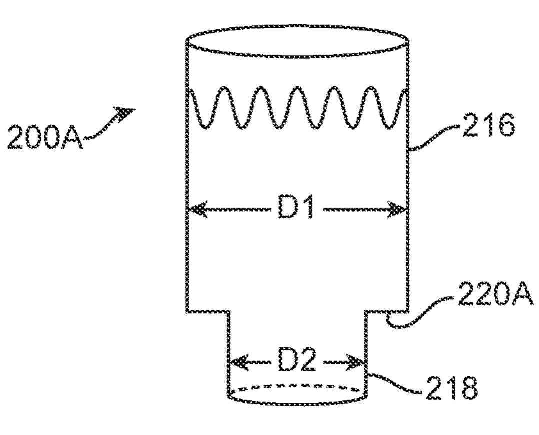
FIG. 3 is a stent-graft having a stepped transition portion in accordance with another embodiment.

FIG. 3 is a stent-graft 200A having a stepped transition portion 220A in accordance with another embodiment. Stent-graft 200A of FIG. 3 is similar to stent-graft 200 of FIGS. 1 and 2 and thus only stepped transition portion 220A is described in detail.

Paying particular attention now to FIG. 3, stepped transition portion 220A is an abrupt step in stent-graft 200A, sometimes called a step function. In accordance with one embodiment, stepped transition portion 220A is an annulus and lies in a plane perpendicular to a longitudinal axis of stent-graft 200A. Accordingly, angles between body portion 216 and stepped transition portion 220A and between stepped transition portion 220A and waist portion 218 are right angle, i.e., are 90° angles. However, in other embodiments, stepped transition portion 220A is shaped as a truncated cone and angles between body portion 216 and stepped transition portion 220A and between stepped transition portion 220A and waist portion 218 are non-right angles, i.e., are greater or less than 90° angles.

Referring now to FIGS. 2 and 3 together, captured proximal portion 316 is located within stent-graft 200A to form an interlock between stent-grafts 200A, 300 in a manner similar to that discussed above.

Figure 4:
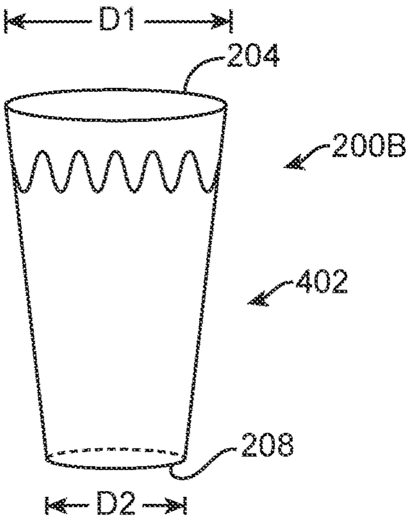
FIG. 4 is a stent-graft having a continuous gradient in accordance with another embodiment.

FIG. 4 is a stunt-graft 200B having a continuous gradient 402 in accordance with another embodiment. Stent-graft 200B of FIG. 4 is similar to stent-graft 200 of FIGS. 1 and 2 and only the significant differences are described in detail.

Paying particular attention now to FIG. 4, continuous gradient 402 is continuous gradient, or change in diameter in stent-graft 200B. For example, stent-graft 200B has diameter D1 at proximal end 204, diameter D2 at distal end 208, and continuously decreases in diameter from proximal end 204 to distal end 208. In one embodiment, proximal end 204 is referred to as body portion 216, distal end 208 is referred to as waist portion 218, and the length of stent-graft 200B between proximal end 206 and distal end 208 is referred to as transition portion 220.

Referring now to FIGS. 2 and 4 together, captured proximal portion 316 is located within stent-graft 200B to form an interlock between stent-grafts 200B, 300 in a manner similar to that discussed above.

While the stent-grafts 200A and 200B shown with respect to FIGS. 3 and 4 have been described as embodiments of the stent grail 200, they may also be alternative embodiments to stent-graft 300. In such embodiments, each stent-graft component would have a large diameter portion and a small diameter portion, with the large diameter portion of the second stent-graft forming the mechanical interlock with the small diameter portion of the first stent-graft. The small diameter portion of the second stent-graft may then continue distally (e.g., not expand to a larger diameter, such as diameter D3 in FIG. 2).

Figure 5:
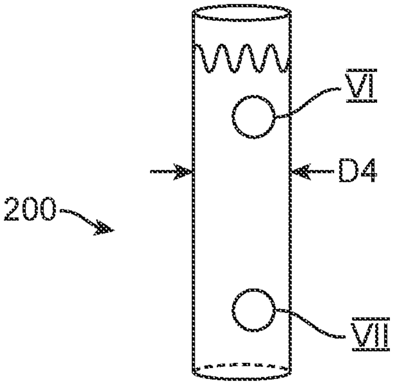
FIG. 5 is a perspective view of the first stent-graft of FIG. 1 in a pre-expansion configuration in accordance with one embodiment.
Figure 6:
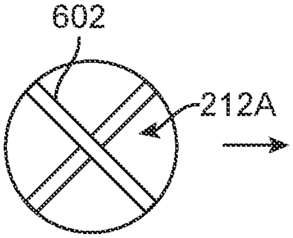
FIG. 6 is an enlarged perspective view of a region VI of the first stent-graft of FIG. 5 in accordance with one embodiment.
Figure 9:
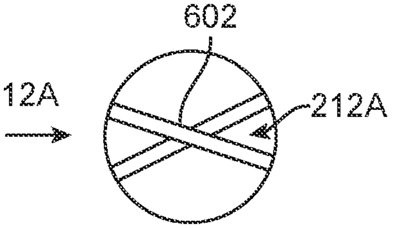
FIG. 9 is an enlarged perspective view of a region IX of the first stent-graft of FIG. 8 in accordance with one embodiment.
Figure 7:
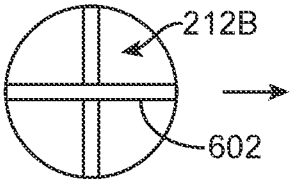
FIG. 7 is an enlarged perspective view of a region VII of the first stent-graft of FIG. 5 in accordance with one embodiment.
Figure 10:
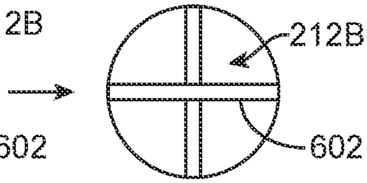
FIG. 10 is an enlarged perspective view of a region X of the first stent-graft of FIG. 8 in accordance with one embodiment.
Figure 8:
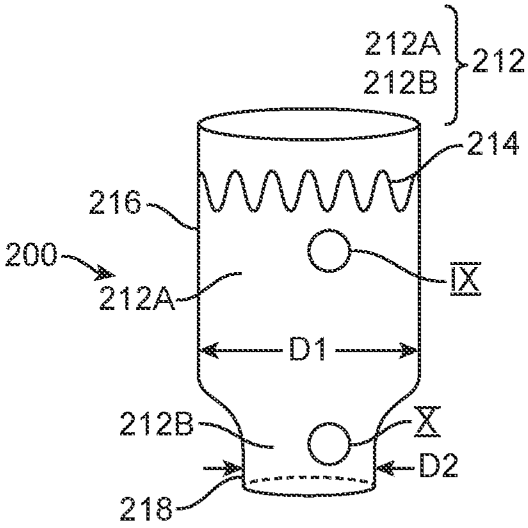
FIG. 8 is a perspective view of the first stent-graft of FIG. 5 in a post-expansion configuration in accordance with one embodiment.

FIG. 5 is a perspective view of stunt-graft 200 of FIG. 1 in a pre-expansion configuration in accordance with one embodiment. FIG. 6 is an enlarged perspective view of a region VI of stent-graft 200 of FIG. 5 in accordance with one embodiment. FIG. 7 is an enlarged perspective view of a region VII of stent-graft 200 of FIG. 5 in accordance with one embodiment. FIG. 8 is a perspective view of stent-graft 200 of FIG. 5 in a post-expansion configuration in accordance with one embodiment. FIG. 9 is an enlarged perspective view of a region IX of stent-graft 200 of FIG. 8 in accordance with one embodiment. FIG. 10 is an enlarged perspective view of a region X of stent-graft 200 of FIG. 8 in accordance with one embodiment.

As illustrated in FIG. 5 when in a pre-expansion configuration, stent-graft 200 is unexpanded. For example, stent-graft 200 is constrained in a delivery system to be in a pre-deployment configuration or stent-graft 200 has been deployed but not yet expanded. Illustratively, stent-graft 200 has a uniform diameter D4 when in the pre-expanded configuration, sometimes called the pre-expansion configuration. However, when in the deployed post-expansion configuration as illustrated in FIGS. 2 and 8, body portion 216 expands relative to waist portion 218 to have a larger diameter D1 and waist portion 218 expands to have diameter D2. In some embodiments, waist portion 218 may not expand. Although stent-graft 200 may have diameter D4 when in the pre-expansion configuration less than diameter D2 in the expanded configuration, generally, stent-graft 200 has diameter D2 or less when in the pre-expansion configuration. The body portion 216 or the waist portion 218 may include a stent ring or rings or may be free of stent rings (e.g., graft material only).

To allow selective expansion of body portion 216, graft material 212 includes first graft material 212A in body portion 216, a second graft material 212B in waist portion 218, and changes from first graft material 212A to second graft material 212B in transition portion 220. First graft material 212A is expandable whereas second graft material 212B is non-expandable, or more generally, first graft material 212A is more expandable than second graft material 212B.

In one embodiment, graft material 212A is sewn or otherwise attached to graft material 212B. In another embodiment, stent-graft 200 is selectively woven such that graft material 212A seamlessly transitions to graft material 212B. In either embodiment, the transition may be a step-change (e.g., abrupt, immediate change) or a gradual change (e.g., a gradient).

For example, as illustrated in FIG. 6, first graft material 212A includes woven graft material that has angled yarns 602, i.e., warp and weft, that have a 45° orientation, more generally a 15° to 45° orientation, in one embodiment a 30° to 60° orientation, and in another embodiment, a 15° to 75° orientation. As shown in FIG. 9, due to the non-perpendicular orientation of yarns 602, yarns 602 can move relative to one another towards a 0° orientation allowing first graft material 212A and body portion 216 to expand.

In contrast, as illustrated in FIG. 7, second graft material 212B includes woven graft material that has perpendicular yarns 602 that have a 0° orientation or more generally a 0° to 15° orientation. In accordance with this embodiment, yarns 602 remain in the 0° orientation to prevent expansion of waist portion 218 as illustrated in FIG. 10.

Although body portion 216 is discussed above as being selectively expandable relative to waist portion 218 by changing the orientation of yarns 602, in other embodiments, body portion 216 is formed of plastically or elastically deformable graft material that is easily deformable with applied pressure to allow the selective expansion as compared to waist portion 218. Plastically deformable graft material may permanently deform and take on a larger diameter, even if the pressure/force is removed (e.g., from a balloon). Elastically deformable graft material may deform in response to a pressure/force but may return (at least partially) to its original shape if all forces are removed. However, if the elastic force is smaller than another force, the elastically deformed material may remain expanded. For example, if a stent ring or rings have a stronger radial force than the elastic force, the graft material may remain in an expanded state. In another embodiment, body portion 216 includes knitted graft material that allows for selective expansion.

While the embodiments of FIGS. 6-9 are described as having a portion that is expandable and a portion that is not expandable (or less expandable), in other embodiments the entire stent-graft may be formed of expandable materials but only a certain portion thereof is expanded. For example, only a portion of the stent-graft may be pressurized (e.g., by a balloon or a self-expanding stent) such that only that portion expands and other portions do not expand (or expand less), even if capable of doing so. Accordingly, the whole stent-graft may be formed of a graft material such as shown in FIG. 6, but only a portion of it will be expanded such that is resembles FIG. 9. This may apply to any of the expansion mechanisms described herein.

Multiple examples of stent-grafts having expandable portions are described above. The expansion of any of these examples may be performed using a variety of methods or approaches. One example may include balloon expansion of the stent graft including the expandable portion. The balloon expansion may take place during deployment of the stent-graft or post deployment (or both). For example, if the stent-graft is a balloon-expandable stent-graft, then the expansion may occur during the deployment of the stent-graft. When deployed, the expandable portion (e.g., body portion 216) may expand to a greater degree than other portion(s) of the stent-graft, due to having different yarn orientation, plastically deformable graft material, elastically deformable graft material, or other mechanisms.

If the stent-graft with the expandable portion is not a balloon expandable stent (in terms of deployment method), it may still be expanded by a balloon after its initial deployment. For example, it may be ballooned in a separate, isolated step after deployment or it may be ballooned as part of the deployment of another stent-graft (e.g., stent-graft 300 may be a balloon expandable stent-graft). Accordingly, the balloon expansion may occur indirectly, in the sense that the pressure is transferred through another stent-graft and the balloon doesn't directly contact the expanding portion. The ballooning may be done in a target area to expand just the expandable portion or it may be performed along portions that are expandable and non-expandable and the non-expandable portions may resist or restrict expansion such that the expandable portion is expanded and the non-expandable portion(s) are not (or to a lesser degree).

The stent-graft having the expandable portion may be a self-expanding stent-graft. In these examples, the self-expanding stent rings may provide the pressure/force to expand the expandable portion. In one embodiment, the stent ring or rings in the expandable portion may have a greater radial force than the stent rings in the non-expanding portion. These stent ring(s) may therefore provide the force necessary to stretch the oriented graft material (e.g., FIG. 9), to plastically deform the graft material, or to elastically deform the graft material and overcome its elastic force to stay in an expanded state. In other embodiments, a combination of self-expanding stents and ballooning may be used to expand the expandable portion. For example, the stent-graft may be deployed like a standard self-expanding stent-graft and then a balloon may selectively further expand a portion of the stent-graft—by deforming the stent rings in the expandable area and/or expanding the graft material of the stent-graft.

Figure 11:
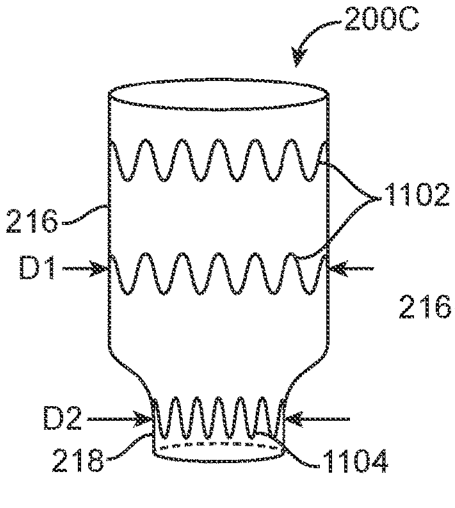
FIGS. 11, 12 are perspective views of stent-grafts in accordance with various embodiments.

FIG. 11 is a perspective view of a stent-graft 200C in accordance with another embodiment. In accordance with this embodiment, diameter D1 of first steak 1102 of body portion 216 is greater than diameter D2 of a second stein 1104 of waist portion 218. By using different diameter stents 1102, 1104, waist portion 218 with a smaller diameter D2 than diameter D1 of body portion 216 is achieved.

Although first stents 1102 are illustrated and discussed, in another embodiment, only second stem 1104 at waist portion 218 is used. Generally, second stent 1104 prevents expansion of waist portion 218 or returns to diameter D2 once the applied pressure is released.

Figure 12:
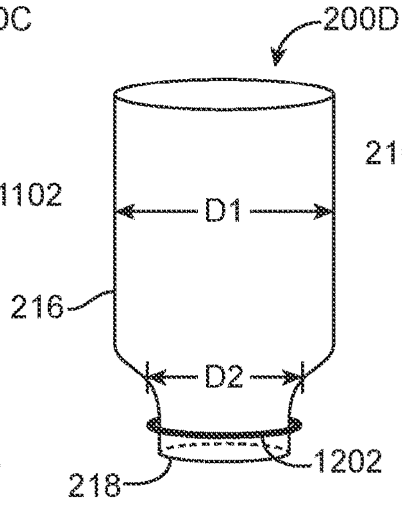

FIG. 12 is a perspective view of a stent-graft 200D in accordance with another embodiment. In accordance with this embodiment, waist portion 218 includes a ring 1202 having diameter D2. Illustratively, ring 1202 is a radiopaque marker band, a suture loop, a plastic ring, or a metal ring that does not deform with applied pressure. By using ring 1202, waist portion 218 with a smaller diameter D2 than diameter D1 of body portion 216 is achieved.

Figure 13:
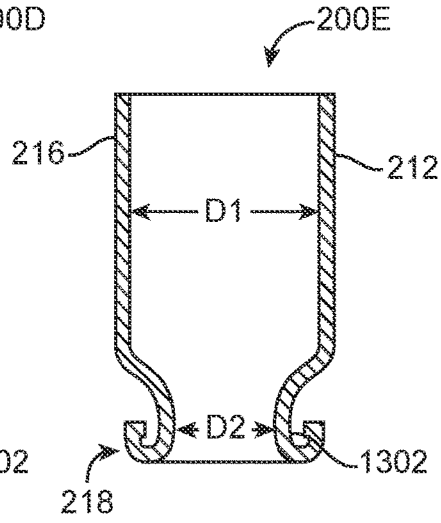
FIG. 13 is a cross-sectional view of a stent-graft in accordance with one embodiment.

FIG. 13 is a cross-sectional view of a stent-graft 200E in accordance with another embodiment. In accordance with this embodiment, waist portion 218 includes a double fabric layer 1302 having diameter D2. Illustratively, graft material 212 of stent-graft 200E is folded back upon itself and bonded or seamed together in waist portion 218 to create double fabric layer 1302. Double fabric layer 1302 has more strength, and thus less expandability, than the single layer of graft material 212 in body portion 216. By using double fabric layer 1302, waist portion 218 with a smaller diameter D2 than diameter D1 of body portion 216 is achieved.

In another embodiment, instead of having a double fabric layer 1302, a thickness of graft material 212 is greater in waist portion 218 than in body portion 216. In yet another embodiment, graft material 212, e.g., non-expandable graft material, is formed with different diameters D1, D2 in waist portion 218 and body portion 216, respectively.

Figure 14:
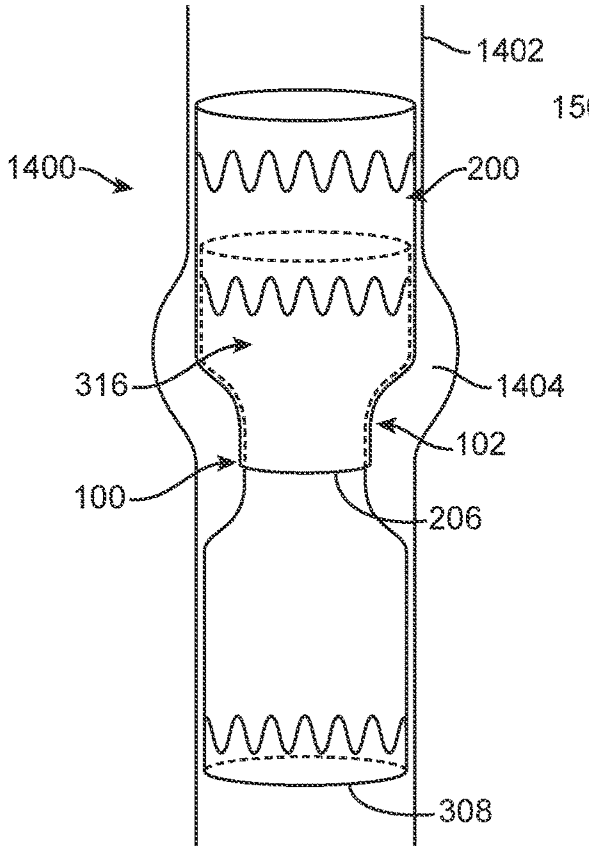
FIG. 14 is a vessel assembly include the modular assembly of FIGS. 1 and 2 in accordance with one embodiment.

FIG. 14 is a vessel assembly 1400 include modular assembly 100 of FIGS. 1 and 2 in accordance with one embodiment. Referring to FIGS. 1 and 14 together, stent-graft 200 is deployed within a vessel 1402 having a diseased portion 1404, e.g., an aneurysm. Stent-graft 200 is secured within vessel 1402.

After deployment of stent-graft 200, a delivery system containing stent-graft 300 is advanced into stent-graft 200 through distal opening 206. Stent-graft 300 is deployed such captured proximal portion 316 of stent-graft 300 is located within stein-graft 200. Distal end 308 of stent-graft 300 is secured within vessel 1402. Mechanical interlock structure 102 mechanically interlocks stent-graft 300 to stent-graft 200 as discussed above.

Modular assembly 100 including stent-grafts 200, 300 spans and thus excludes diseased portion 1404 of vessel 1402.

In one embodiment, stent-graft 200 is a self-expanding stent-graft and stent-graft 300 is a balloon expanded stent-graft. By totaling mechanical interlock structure 102, mating of balloon expandable stent-graft 200 to self-expanding stent-graft 300 is possible even though stent-grafts 200, 300 having different stent-graft properties.

Figure 15:
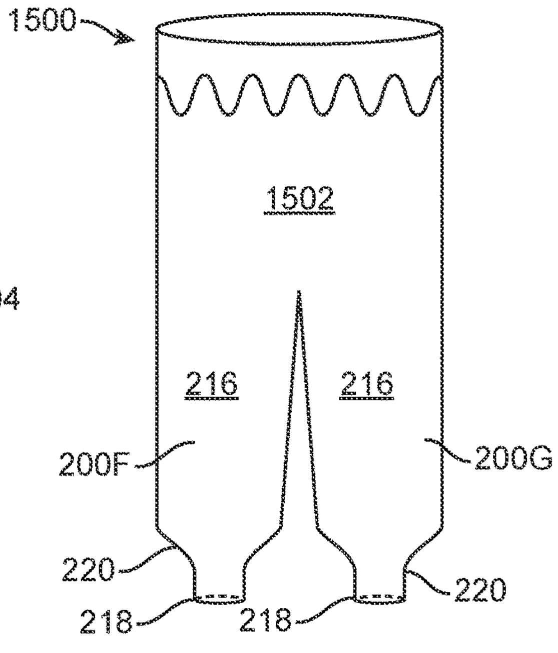
FIG. 15 is a perspective view of a bifurcated stent-graft having two branch limbs in accordance with one embodiment.
Figure 16A:
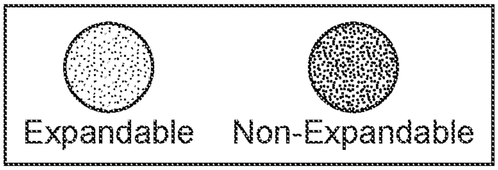
FIGS. 16A, 16B, 16C, 16D, 16E, 16F, 16G, 16H, 16I, 16J, 16K, 16L are perspective view of stent-grafts in accordance with various embodiments.
Figure 16A:
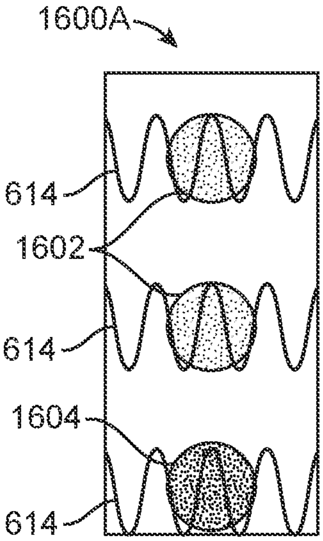
Figure 16B:
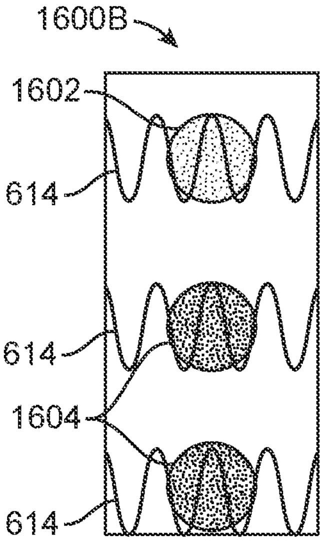
Figure 16C:
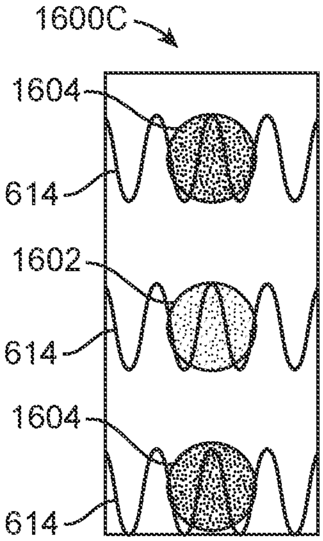
Figure 16D:
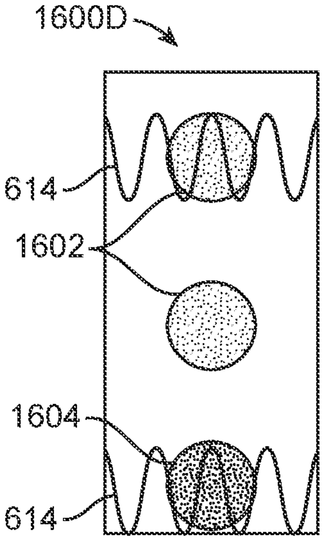
Figure 16E:
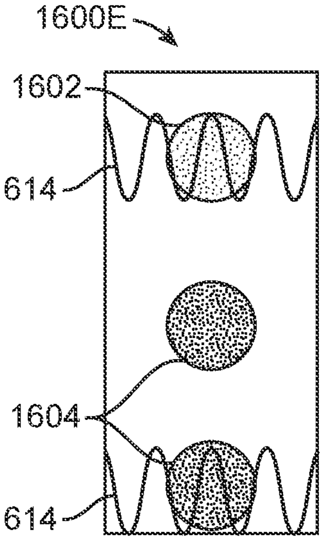
Figure 16F:
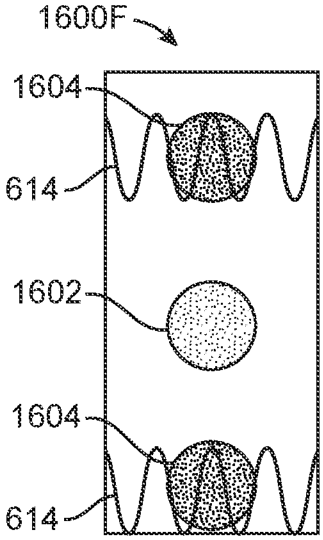
Figure 16G:
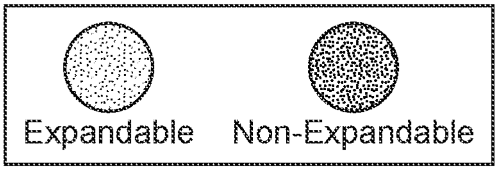
Figure 16G:
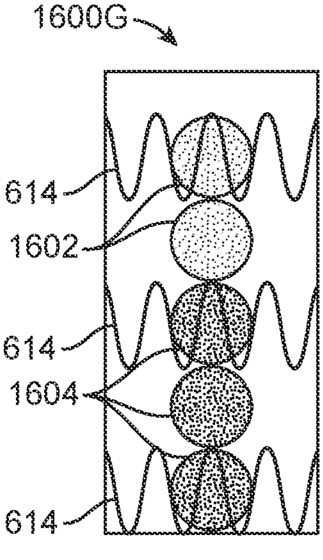
Figure 16H:
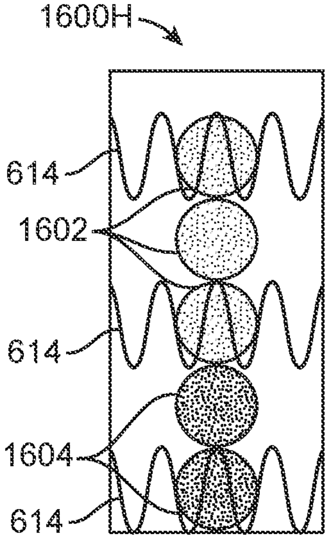
Figure 16I:
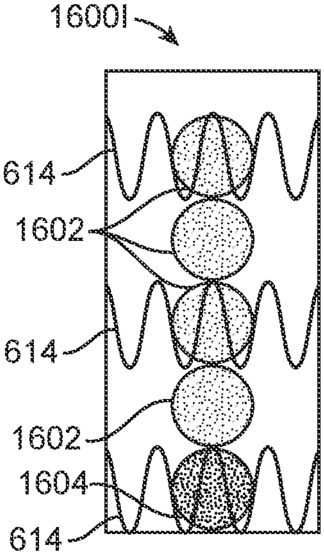
Figure 16J:
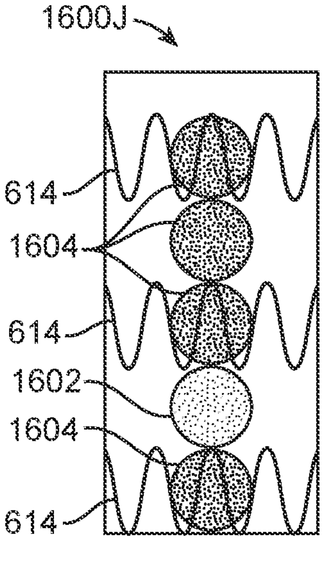
Figure 16K:
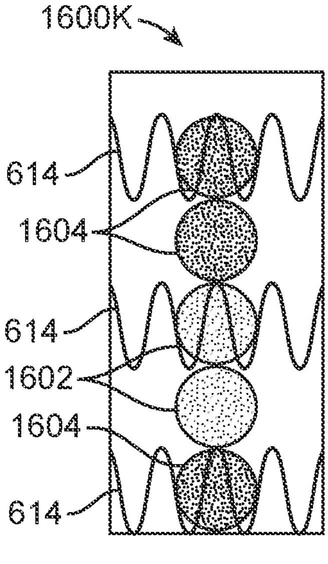
Figure 16L:
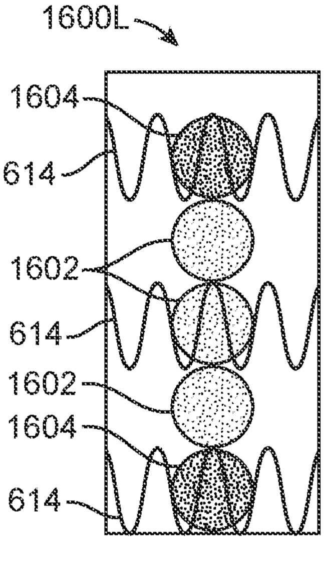

FIG. 15 is a perspective view of a bifurcated stein-graft 1500 having two branch limbs 200F, 200G in accordance with one embodiment. In accordance with this embodiment, each branch limb 200F, 200G is similar to gent-graft 200 having body portion 216, waist portion 218, and transition portion 220 as discussed above. While this embodiment shows both limbs as having a waist and transition portion, in other embodiments one limb may have them and one limb may not. A stent-graft 300 may be coupled to each branch limb 200F, 200G as discussed above.

However, in accordance with this embodiment, proximal ends of each branch limb 200F, 200G is attached to a main portion 1502 of bifurcated stent-graft 1500. Generally, main portion 1502 has a single lumen that is bifurcated into branch limbs 200F, 200G. Although bifurcated stent-graft 1500 is described as being bifurcated, in other embodiments, a main portion 1502 is split into three, four, or more branch limbs similar to branch limbs 200F, 200G. As described above, if there are multiple limbs, any or all may have a waist and transition portion.

While the mechanical interlocking has been generally described herein as a distal stent-graft locking with a proximal stent-graft to prevent distal movement of the distal stent-graft, it should be understood that the same principles may be applied in the opposite direction to prevent proximal movement of a proximal stent-graft. Accordingly, the arrangement of FIG. 2, FIG. 14, etc. could be flipped vertically such that the expanded portion is below/distal to a waist region. This orientation may be useful in situations where there is a proximal or upward force on two connected stent-grafts, for example, in stent-graft systems in the aortic arch with extensions into the great vessels (e.g. left subclavian, left carotid, and brachiocephalic).

FIGS. 16A, 16B, 16C, 16D, 16E, 16F, 16G, 16H, 16I, 16J, 16K, 16L are perspective view of stent-grafts 1600A, 1600B, 1600C 1600D 1600E, 1600F, 1600G, 1600H, 1600I, 1600J, 1600K, 1600L, respectively, in accordance with various embodiments. Stent-grafts 1600A, 1600B, 1600C, 1600D, 1600E, 1600F, 1600G, 1600H, 1600I, 1600J, 1600K, 1600L are similar to stent-graft 200 of FIG. 1 except that locations of expandable sections 1602 and non-expandable sections 1604 are located at different locations upon the stent-grafts depending upon the embodiment.

FIGS. 16A-16L illustrate multiple configurations with at least one non-expandable section 1604 being at the end of the modular connection region that exits towards the component being introduced. The non-expandable section 1604 is on the distal side or the proximal side depending on the direction in which the modular connection is being built. The length of an expandable section 1602 and a non-expandable section 1604 may vary and the expandable section 1602 may be in between non-expandable section 1604. The expandable section 1602 may or may not have a stent 614 within its region. Although the expandable sections 1602 and the non-expandable sections 1604 are illustrated as circles in FIGS. 16A-16L, it is understood that the circles represent sections at particular longitudinal locations and that these sections extend around the entire circumference.

In addition to increased modular connection strength (resist component migration or joint separation) the use of an expandable section 1602 in conjunction with a non-expandable section 1604 can improve the hemodynamic flow. Reducing the amount of shear-stress and turbulence reduces the risk for limb occlusion, flow obstruction leading to ischemic, or clot embolization. The design can reduce blood flow shear stress and turbulence by reducing the amount of oversizing required to achieve modular connections (this yields a smoother lumen by minimizing the amount of material need to create a the junction).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A method comprising:

deploying a first stent-graft within a vessel such that a body portion of the first stent-graft has a first diameter and a waist portion of the first stent-graft has a second diameter less than the first diameter, the body portion of the first stent-graft transitions into the waist portion of the first stent-graft through a transition portion of the first stent-graft, the waist portion of the first stent-graft has a distal end; and deploying a proximal portion of a second stent-graft within the first stent-graft proximal to the waist portion of the first stent-graft to capture the proximal portion of the second stent-graft within the first stent-graft, the proximal portion of the second stent-graft has a proximal end, the proximal portion of the second stent-graft follows a profile of the body portion, the transition portion, and the waist portion of the first stent-graft from the proximal end of the proximal portion of the second stent-graft to the distal end of the waist portion of the first stent-graft, the second stent-graft has a distal portion extending distally from the proximal portion of the second stent-graft, the distal portion of the second stent-graft having a waist portion, the waist portion of the distal portion of the second stent-graft transitions, distally from the distal end of the waist portion of the first stent-graft, into a body portion of the distal portion of the second stent-graft through a transition portion of the distal portion of the second stent-graft, the body portion of the distal portion of the second stent-graft has a third diameter greater than a fourth diameter of the waist portion of the distal portion of the second stent-graft;

wherein the body portion of the first or second stent-graft is expanded more than the waist portion of the first or second stent-graft, respectively, during the deploying of the first or second stent-graft.

2. The method of claim 1 wherein the body portion of the first stent-graft is selectively expandable relative to the waist portion of the first stent-graft.

3. The method of claim 1 wherein the deploying the first stent-graft comprises pressurizing the first stent-graft to cause the expansion.

4. The method of claim 1 wherein the proximal portion of the second stent-graft includes a seated portion.

5. The method of claim 4 wherein an interlock between the first stent-graft and the second stent-graft is created by locating the seated portion of the second stent-graft proximal to the waist portion of the first stent-graft.

6. The method of claim 1 wherein the body portion of the first or second stent-graft comprises first graft material having angled yarns.

7. The method of claim 6 wherein the waist portion of the first or second stent-graft comprises second graft material having perpendicular yarns.

8. The method of claim 1 wherein a diameter of the transition portion of the first stent-graft is less than the first diameter and greater than the second diameter.

9. The method of claim 1 wherein the transition portion of the first stent-graft has a varying diameter transitioning from the first diameter at the body portion of the first stent-graft to the second diameter at the waist portion.

10. The method of claim 1 wherein the body portion extends distally from a proximal end of the first stent-graft to the transition portion, and the waist portion extends proximally from a distal end of the first stent-graft to the transition portion.

11. The method of claim 1 wherein the waist portion of the first stent-graft has a longitudinal length.

* * * * *